United States Patent [19]

Disteldorf et al.

[11] 4,429,157

[45] Jan. 31, 1984

[54] PROCESS FOR THE PREPARATION OF PRIMARY MONO- AND DIAMINES FROM OXO COMPOUNDS

[76] Inventors: Josef Disteldorf, Am Sengenhoff 2a; Werner Hübel, Birnenbruchstrasse 34, both of 4690 Herne 1; Lothar Broschinski, Lüenbrink, 18,4760 Werl, all of Fed. Rep. of Germany

[21] Appl. No.: 272,386

[22] Filed: Jun. 10, 1981

[30] Foreign Application Priority Data

Jun. 12, 1980 [DE] Fed. Rep. of Germany ....... 3021955

[51] Int. Cl.$^3$ .............................................. C07C 85/08
[52] U.S. Cl. .................................. 564/446; 564/448; 564/462; 564/396; 564/397; 564/398; 549/480; 546/244
[58] Field of Search ............... 564/446, 448, 462, 396, 564/397, 398; 549/480; 546/244

[56] References Cited

U.S. PATENT DOCUMENTS 3,565,954 2/1971 Bouniot ........................... 564/446 X
4,129,597 12/1978 Thompson ..................... 564/446 X

*Primary Examiner*—Paul F. Shaver
*Attorney, Agent, or Firm*—Oblon, Fisher, Spivak, McClelland & Maier

[57] ABSTRACT

Primary amines and/or diamines can be prepared from oxo compounds, optionally containing additional reducible groups, by a process comprising:

(1) reacting the oxo compound with ammonia in the presence of an imine-forming catalyst, preferably an ion exchanger loaded with ammonia ions, at a temperature of 10° to 120° C. and a pressure of 1 to 300 bar, whereby a Schiff base is formed; and
(2) reducing the Schiff base by reaction with ammonia and hydrogen in the presence of a hydrogenation catalyst.

29 Claims, No Drawings

PROCESS FOR THE PREPARATION OF PRIMARY MONO- AND DIAMINES FROM OXO COMPOUNDS

BACKGROUND OF THE INVENTION

1. Field of the Invention

The invention relates to an improvement in the process for preparing primary mono- and diamines by reductive amination of oxo compounds, optionally containing other reducible groups or functions, such as C=C double bonds, nitrile (and nitro) groups, by a preliminary treatment with ammonia in the presence of catalysts loaded with ammonium ions.

The term "oxo compounds" indicates, as usual, compounds containing carbonyl groups, particularly aldehydes and ketones.

2. Description of the Prior Art

It is already known that saturated and unsaturated aldehydes and ketones can be converted into primary amines with ammonia and hydrogen under elevated pressure and at elevated temperatures using suitable catalysts, for example, those having cobalt and/or nickel and/or iron as the principal components.

The reductive amination of compounds having a low molecular weight and a simple structure is actually accomplished in a comparatively satisfactory manner, but with compounds having higher molecular weight, complex structure or several functional groups a comparatively low space velocity is frequently observed. In that case also, the life of the catalyst is frequently unsatisfactory. These two characteristics are affected by a rather extensive formation of by-products, particularly when the formation of cyclic structures is favored. Such by-products not only reduce the yield of the reaction but often significantly reduce the overall yield because of difficulties in workup or purification of the desired amines. Yields below 80%, sometimes even below 50%, are observed, for example, in the production of benzylamine from benzaldehyde, furfurylamine from furfuryl alcohol, pentanediamine from the corresponding cyanoaldehydes, 3,3,5-trimethylcyclohexylamine (TMCA) from isophorone (3,5,5-trimethyl-2-cyclohexen-1-one) or 2,2,6,6-tetramethyl-4-aminopiperidine (triacetonediamine, TAD) from 2,2,6,6-tetramethyl-4-piperidone (triacetoneamine, TAA) and, particularly, in the production of 3-(aminomethyl)-3,5,5-trimethylcyclohexylamine (isophoronediamine, IPD) from 3-cyano-3,5,5-trimethylcyclohexanone (isophoronenitrile, IPN). In the last mentioned reaction, for example, there are formed not only the by-product 3-(aminomethyl)-3,5,5-trimethylcyclohexanol (isophoroneamino alcohol, IPAA), but a large number of by-products arising from elimination of HCN, cyclization, side reactions and further reactions of intermediate products. A mixture of compounds, characterized as the so-called peak 7 in gas chromatography, can be separated only with especially great difficulty. This mixture of compounds causes a distillation loss of approximately 1% IPD per 0.1% of the peak 7 mixture in the purification of IPD to the specifications prescribed, for example, for the production of polyamides. Similar undesirable by-products also arise in the reductive amination of other oxo compounds. Accordingly, there has been a need to find a procedure by which the desired amines would be obtained in a distinctly higher yield and at the same time by a process which would be economical on industrial scale.

SUMMARY OF THE INVENTION

Surprisingly, this objective could be achieved by converting the appropriate oxo compound first into a Schiff base with ammonia in the presence of a catalyst and, subsequently, subjecting the thus obtained intermediate product to the usual reductive amination. The conversion of the oxo compound into the Schiff base proceded sufficiently rapidly with the help of imine-forming catalysts. Inorganic or organic ion exchangers loaded with ammonium ions are particularly suitable for this purpose. The catalytically active ammonium form of the ion exchangers can be obtained by prior loading of the ion exchangers with ammonia or amines or by the action of ammonia or amines during the preliminary reaction according to the invention. The use of easily soluble ammonium salts, such as ammonium formates, acetates or chlorides, as imine-forming catalysts proved to be inexpedient since, in that case, considerable losses were incurred in the subsequent reductive amination.

Ammonium salts insoluble in the reaction mixture, such as, for example, ammonium sulfate, can also be used as imine-forming catalysts in crystalline form or precipitated on carriers.

DETAILED DESCRIPTION OF THE INVENTION AND PREFERRED EMBODIMENTS

The preliminary reaction according to the invention between the oxo compound and ammonia is carried out in the presence of one of the above mentioned imine-forming catalysts at temperatures of 10° to 120° C., preferably at 15° to 70° C., under autogenous or elevated pressure.

For the reaction of IPN with ammonia, for example, an equilibrium arises in the reaction which forms the Schiff base (SB) according to the following formula:

$$IPM + NH_3 \rightleftharpoons SB + H_2O$$

The equilibrium constant K is then

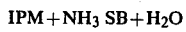

$$K = \frac{[IPN][NH_3]}{[SB][H_2O]}$$

This indicates that the conversion of an oxo compound into the Schiff base can be favored by excess $NH_3$ as well as the removal of water. If it is desirable to separate the reaction water in order to influence the equilibrium, then it is expedient to keep the ammonia excess low. A mole ratio IPN:$NH_3$ such as 1:1.3 to 3 is advisable in this case. This mode of operation is favorable for the phase separation while $NH_3$ in greater excess acts as a solubilizer and thus hinders the separation of aqueous and organic phases.

In order to facilitate the phase separation, water and/or an inert organic solvent can also be added. Not only is the equilibrium favorably influenced by the separation of the ammoniacal aqueous phase but also a higher catalyst load is made possible in the hydrogenation.

The process is technically simpler when $NH_3$ is kept in great excess right from the beginning. A rather large $NH_3$ excess is customary, anyway, in the reductive amination in order thereby to suppress secondary reactions, such as, for example, the formation of secondary amine groups. The formation of the Schiff base is favored by the NH$_3$ excess in the preliminary reaction according to the invention. Furthermore, the reaction mixture remains homogeneous under these conditions, and the entire process can take place without intermediate operations.

The reaction of the oxo compound with ammonia can be carried out under autogenous pressure. This embodiment is particularly advisable when a phase separation is to be effected.

However, the preliminary reaction can also be performed at a higher pressure, for example, at 300 bar. This method is preferred when using excess NH$_3$ and particularly when the preliminary reaction and the reductive amination are to be performed in immediate sequence. After the preliminary reaction, the reductive amination is carried out under the usual conditions, i.e. with excess of ammonia and hydrogen at elevated temperature and pressure, generally at 80° to 200° C. and 80 to 300 bar. As catalysts for these reactions, the known compounds and metals of the Group VIII of the Periodic Table can be used as well as chromium, manganese, copper, zinc, molybdenum, tungsten, rhenium and Cu-chromite, but particularly cobalt, nickel, iron and the platinum metals.

The process of the invention for preparing primary amines and/or diamines from oxo compounds, particularly of 3-aminomethyl-3,5,5-trimethylcyclohexaneamine (isophorone diamine, IPD) from 3-cyano-3,5,5-trimethylcyclohexanone (isophoronenitrile IPN), is thus characterized in that, before reaction with ammonia and hydrogen in the presence of hydrogenation catalysts, the oxo compounds are subjected to a preliminary reaction with ammonia in the presence of imine-forming catalysts at temperatures of 10° to 120° C., preferably at 15° to 70° C., and under pressures of 1 to 300 bar. Of course, the process can be performed all together or in partial steps, for example, preliminary reaction, water separation, hydrogenation. It can be carried out batchwise as well as by a continuous process. Moreover, the preliminary reaction as well as the hydrogenation can be carried out using a tank or spray process as described. However, the preliminary reaction is preferably carried out by a tank process, i.e. with flooded catalyst, while the hydrogenation is preferably done by a spray process.

As to the combination of the preliminary reaction and the hydrogenation, both steps can be performed in separate reactor vessels as well as in a single reactor optionally divided into several sections. Two reactor vessels are advantageous when alternative embodiments of the process involving phase separation are carried out.

When great excess of ammonia is used already in the preliminary reaction, the process can even be carried out in a single reactor. In this case, the imine-forming catalyst can be arranged either as a separate layer of the catalyst bed or as a mixture with the hydrogenation contact. Thus, the formation of the Schiff base as well as the reductive amination are performed in the "single reactor" in sequence. In this instance, temperature and pressure of the reactor sections can be adjusted, as desired, to the respective optimum conditions for formation of the Schiff base or the reductive amination, respectively.

Depending on whether the separation of an aqueous phase or ammonia excess is preferred in order to favor the formation of the Schiff base, or whether two or only one reactor are used, the following alternatives, among others, are possible for the process of the invention.

(1) A volumetric ratio, oxo compounds: NH$_3$, of 1:0.5 to 20 is chosen in the preliminary reaction and the homogeneous reaction mixture is immediately subjected to the reductive amination, after adding, if necessary, enough ammonia to produce a volumetric ratio, oxo compounds: NH$_3$, of 1:10 to 20.

(2) A volumetric ratio, oxo compound: NH$_3$, of 1:1.3 to 3 is chosen for the preliminary reaction, the aqueous-ammoniacal phase is separated and the organic phase is subjected to the reductive amination after enough ammonia is added to produce a volumetric ratio, oxo compound: NH$_3$, of 1:10 to 20. In order to improve the separation of the aqueous phase from the organic phase, either water and/or inert organic solvents can be added (after the formation of the Schiff base).

A reactor is used wherein the imine-forming catalyst is placed in the first section and the hydrogenation catalyst in the following section, arranged in layers, and a mixture of oxo compound and NH$_3$ is passed through the reactor at a volumetric ratio of 1:10 to 20 to which additional hydrogen is added to reach the required excess at least in the later sections or, optionally, even right from the beginning.

In an analogous manner, the oxo compound-NH$_3$ mixture, can also be passed through a reactor which is charged with a mixture of the imine-forming catalyst and the hydrogenation catalyst, hydrogen being added n the later sections or from the beginning.

The overall yield of the process is determined by the yields of the two stages of the reaction. Both are operated at an optimum if possible. Nevertheless, the optimum of the first process may not always conform with the optimum of the second one. Therefore, if necessary, economic compromises must be made with respect to individual process parameters in the performance of the process, for example, between the size of the preliminary reactor (or the volume ratio between the respective sections in a unitary reactor) and the remaining parameters (temperature, residence time or IPN: NH$_3$ ratio) (see Example 6).

It can be gathered from the general literature on preparation of Schiff bases and reductive amination that the addition of soluble salts, such as ammonium formate or ammonium acetate and ammonium chloride, should have a favorable effect, either by promoting the formation of Schiff bases with sterically hindered carbonyl compounds or by the suppression of the reduction of the oxo compound to the corresponding carbinol. Their effect is essentially due to the adjustment of the pH of the mixture to certain values which are preferred for the water elimination from the initially formed carbonyl-NH$_3$ addition compound (O-N-ketals or acetates) initially. In general, such additives are not used.

From these few indications in the literature, in part appearing only as notes in connection with the preparation of special amines, it could not be concluded that solid materials, insoluble in the reaction mixture and carrying ammonium ions, would have a strong catalytic effect, by heterogeneous catalysis, on the formation of Schiff bases. Thus, it was surprising in the preparation of amines which are otherwise difficult to prepare from the corresponding oxo compounds that the preliminary reaction with NH$_3$, required for the suppression of otherwise unavoidable by-products and lasting for several hours, can be reduced to a few minutes. At the same time, it was possible to considerably reduce the reaction temperature, in some cases down to 10° C. Additionally, the yield of the desired amine was increased by a few percent and the formation of by-products which interfere with the workup and reduce the yield considerably was almost completely suppressed.

Furthermore, the space velocity is increased with an additional refinement of the process wherein the the reaction water is removed. Thus, the process according to the invention does not proceed directly from the oxo compound to the amine or diamine but via the Schiff base. This intermediate compound is obtained with the help of suitable catalysts and undergoes the catalytic reductive amination far more readily than the original oxo compound. The sum of the activation energies for these partial reactions is evidently lower than the activation energy for the direct reaction. Without the presence of the imine-forming catalysts, the Schiff base is not formed fast enough to achieve an industrially satisfactory process for oxo compounds which are otherwise not readily aminated. In summary, the use of the catalyst of the invention not only achieves a considerable increase in the yield but also a simplification of the overall process owing to the reduction in the preliminary reactor volume and distillation requirements for purification. It thus results in considerable economic savings.

The following examples serve to illustrate the character of the invention without thereby limiting it to the scope of the examples.

EXAMPLE 1

(Comparative Example)

Into the top of a hydrogenation reactor charged with 500 ml of commercial cobalt catalyst, 50 ml/h 3-cyano-3,5,5-trimethylcyclohexanone (isophoronenitrile, IPN) and 500 ml/h liquid $NH_3$ are pumped. The reaction system is heated to 120° C. and is maintained at 270 bar with $H_2$. A steady gas flow is started and 100 l/h of water gas are discharged through a separator. The reaction mixture leaving the reactor at the bottom passes through a cooler into the separator, and the liquid phase is fed to a pressurized column where the excess $NH_3$ is distilled off. The crude diamine is withdrawn from the column sump for further processing. The crude diamine obtained in this way contains practically no residual IPN, and the conversion is thus complete. The yield of 3-aminomethyl-3,5,5-trimethylcyclohexylamine (isophoronediamine, IPD) amounts to only 48.3% by gas chromatographic analysis. The greater portion consists predominantly of 3-aminomethyl-3,5,5-trimethylcyclohexanol (isophoroneamino alcohol, IPAA) besides 3,3,5-trimethylcyclohexylamine (TMCA); 3,3,5-trimethylcyclohexanol (TMC-ol), 1,3,3-trimethyl-6-azabicyclo[3.2.1] octane (IPD-imine) and a number of unknown compounds, among them, the peak 7 mixture which is difficult to separate.

EXAMPLE 2

(Comparative Example)

A reductive amination is performed in a reaction system as in Example 1 after IPN has first been subjected to a preliminary reaction with 10 times its volume of $NH_3$ for 1.5 hours at 70° C. The IPN conversion is again complete. The IPD yield amounts to 69.5% by gas chromatography. The remainder again consists predominantly of IPAA besides the preliminary fractions listed in the first example and the peak 7 mixture.

EXAMPLE 3

(Comparative Example)

The reductive amination of IPN is conducted according to Example 2 but the preliminary reaction is carried out for 5.5 hours at 70° C. with a volumetric ratio IPN:$NH_3$ of 1:2 with addition of $NH_3$ to the rector to a volume ratio of 1:10. Otherwise the conditions are the same.

The conversion is again complete. The IPD yield amounts to 90.3% by gas chromatography. The remainder consists mainly of the aforementioned preliminary fractions and only about 2% IPAA. However, the unknown peak 7 mixture which is difficult to separate is present in an amount of 0.6%. In order to remove this fraction to the admissible 0.1% for pure IPD, a loss of abut 5% of IPD must be accepted; this decreases the yield of the process to about 85%.

EXAMPLE 4

Using the same experimental arrangement as in Example 3, the process is carried out utilizing a preliminary reactor packed with ion exchanger Lewatit SP 120 and a preliminary reaction of IPN with $NH_3$ in a volume ratio of 1:10 for 6 minutes at 50° C. (in a pipe coil) under otherwise the same conditions.

The conversion is again complete. The IPD yield amounts to 94.7% by gas chromatography. The by-products consist almost exclusively of the preliminary fraction components, IPAA is only present at about 0.10% and the compound which is difficult to separate only in proportions of <0.1%. After the batch distillation of the crude product, 92.0% IPD pure fraction remains besides 6.4% fore run and 1.6% tailings and residue.

EXAMPLE 5

Using the same experimental arrangement as in Example 4, the preliminary reaction of IPN with $NH_3$ in a volume ratio of 1:2 is carried out for 20 minutes at 50° C. (in a pipe coil). The hydrogenation is carried out subsequently after more $NH_3$ is added up to a volume ratio of 1:10.

The conversion is again complete and the IPD yield amounts to 94.6% by gas chromatography. The by-products consist almost exclusively of preliminary fractions, only 0.12% of IPAA is present and the peak 7 compound which is difficult to separate, only in proportions less than 0.1%. The batch distillation of the crude product afforded the same results as in Example 4.

EXAMPLE 6

In the following experiments, the $NH_3$: IPN ratio or the residence time and temperature were varied several times within the given limits in the course of 70 days of running using preliminary reactors of 4 different volumes.

Thus, at least 2 experiments were carried out in the given temperature ranges, i.e. those at the listed temperature limits. However, in most cases additional experiments were run at fixed temperatures within the given range.

| Preliminary reactor residual volume ml | Mole ratio $NH_3$:IPN | Residence time (min) | Temperature (°C.) |
| --- | --- | --- | --- |
| 443 | 20 | 25 | 45–60 |
|  | 10 | 48 | 50–60 |

| Preliminary reactor residual volume ml | Mole ratio NH$_3$:IPN | Residence time (min) | Temperature (°C.) |
|---|---|---|---|
|  | 5 | 89 | 45–60 |
|  | 2 | 25 | 45–60 |
| 50 | 10 | 5.5 | 50–70 |
|  | 2 | 2 | 50–85 |
| 20 | 10 | 2.2 | 50–70 |
|  | 2 | 8 | 50–70 |
| 10 | 2 | 4 | 50–70 |

IPD yields after the main reaction of about 95% by gas chromatography were always observed in the experiments with residence times of >4 minutes in the preliminary reactor and reaction temperatures above 50° C. In all cases, the IPAA fraction was always <0.5% and the fraction of the substance which is difficult to separate was always <0.15%.

Lower IPD yields were found in experiments outside these limits.

EXAMPLE 7

As in the preceding examples, a hydrogenation reactor (shaft furnace type 1.2 liters volume) was packed with 500 ml of commercially available cobalt catalyst. Separated therefrom by means of an intermediate layer of inert packing material and superimposed a wire screen, a packing is formed from an ion exchanger (250 ml bulk volume). The reaction system is kept at a maximum temperature of 120° C. in the lower range and at only 50° to 70° C. in the upper range by means of 2 separate heating elements. 50 ml/h IPN and 500 ml/h liquid NH$_3$ are pumped into it from the top. By pressurizing with H$_2$ to 270 bar, the system is maintained under pressure whereby 200 l/h exhaust gas are discharged through a separator. The reaction mixture leaving the reactor through the bottom enters the separator through a cooler while the liquid phase is introduced into a pressurized column where the excess ammonia is distilled off. The crude diamine is withdrawn from the column sump and directed to further processing. It contains no residual IPN, thus the conversion is complete. The yield amounts to 94.1% by gas chromatography; <0.3% IPAA is still present and <0.15% of the substance which is difficult to separate.

EXAMPLE 8

500 g powdered IPN (=3.03 moles) together with 100 ml acid ion exchanger Lewatit SP 120 are placed into an autoclave equipped with a lift stirrer. After purging with N$_2$, 125 ml of liquid NH$_3$ (=4.5 moles) are introduced under pressure. The temperature rises from 15° to 22° C. and the stirrer is stopped. After further heating, the stirrer can be operated again after 40° C. is reached. The temperature increases to 65° C. owing to evolved heat. At the same time, the pressure drops from 7.2 bar to 5.0 bar; the residual pressure corresponds approximately to the excess pressure of N$_2$ with which the liquid ammonia was compressed into the autoclave. After a reaction period of half an hour, the autoclave is cooled and depressurized; in this procedure only a little NH$_3$ escapes. The contents of the autoclave remain liquid at room temperature. The ion exchanger is separated from the liquid phase which is transferred to a phase separator where it is freed of a small portion of an acqueous phase. The remaining oily, organic phase is initially liquid but starts to crystallize if left standing for some time. However, by heating it to 40° C., it is kept liquid. In this form, it is continuously hydrogenated in a hydrogenation furnace packed with cobalt with the addition of 10 volumes of liquid NH$_3$. In this reaction the same temperature and pressure conditions are maintained as in the preceding examples.

The conversion is again complete; only when increasing the catalyst charge by 50% compared with the preceding examples, aminonitrile starts to break through as revealed by gas chromatography (GC). The IPD yield amounts to 93.9%, the IPAA proportion is <0.5% and that of the compound which is difficult to separate below 0.15%.

EXAMPLE 9

(Comparison Example)

Using the same test arrangement as in Example 1, triacetoneamine (TAA) is converted into triacetonediamine (TAD) by means of reductive amination. For this purpose, 150 ml/h of starting material, which contains 30.5% low boiling fractions, 58.9% TAA and 10.6% higher boiling fractions, are pumped, together with 300 ml/h of liquid NH$_3$, into the reactor which is heated to 130° C. and is maintained at a pressure of 270 bar with H$_2$. A gas flow is established whereby 150 l/h of exhaust gas are discharged through the separator.

The reaction mixture freed of excess NH$_3$ contains 34.9% low boiling feactions, 27.6% TAD, 9.1% intermediate product, 27.7% TAA-aminoalcohol and 5.7% higher boiling substances according to GC analysis. With a complete TAA conversion, a TAD yield of 47.0% was obtained (calculated on the TAA content of the starting material).

EXAMPLE 10

Using the same test arrangement as in Example 4, i.e. with the utilization of a preliminary reactor packed with ion exchanger Lewatit SP 120, the starting material, as in the preceding example, and liquid NH$_3$ are subjected to a preliminary reaction at a TAA: NH$_3$ volume ratio corresponding approximately to 1:4 at 70° C. with a residence time of 5 minutes and subsequently reductively aminated.

After having removed the excess NH$_3$ is removed, the reaction product contains 30.7% low boiling materials, 56.1% TAD, 8.2% intermediate products, 2.3% TAA-aminoalcohol and 2.7% higher boiling substances according to the GC analysis. Thus, with a complete TAA conversion, a TAD yield of 95.2% was obtained (relative to the TAA content of the starting material).

We claim:

1. A process for preparing primary amines comprising:
    (1) reacting an oxo compound with ammonia in the presence of an imine-forming catalyst at a temperature of 10° to 120° C. and a pressure of 1 to 300 bar, whereby a Schiff base is formed; and
    (2) reducing said Schiff base by reaction with ammonia and hydrogen in the presence of a hydrogenation catalyst,
    wherein said imine-forming catalyst is an ion exchanger loaded with ammonium ions.

2. The process of claim 1 wherein said ion exchanger is an inorganic ion exchanger.

3. The process of claim 1 wherein said ion exchanger is an organic ion exchanger.

4. A process for preparing primary amines comprising:

(1) reacting an oxo compound with ammonia in the presence of an imine-forming catalyst comprised of an ammonium salt which is insoluble in the reaction mixture at a temperature of 10° to 120° C. and a pressure of 1 to 300 bar, whereby a Schiff base is formed; and (2) reducing said Schiff base by reaction with ammonia and hydrogen in the presence of a hydrogenation catalyst.

5. The process of claim 4 wherein said ammonium salt is supported on a carrier.

6. The process of claim 4 or claim 5 wherein said ammonium salt is ammonium sulfate.

7. The process of claim 1 wherein in step (1) said oxo compound is in the gas phase and the volume ratio of ammonia to oxo compound is from 1:0.5 to 1:20 whereby a reaction mixture containing a Schiff base is produced; and in step (2) the volume ratio of ammonia to said reaction mixture is from 1:10 to 1:20.

8. The process of claim 7 wherein the reaction mixture produced in Step (1) is a homogeneous mixture and said homogeneous mixture is immediately subjected to the process of Step (2).

9. The process of claim 1 wherein in Step (1) said oxo compound is in the liquid phase and the mole ratio of ammonia to said oxo compound is from 1:1.3 to 1:3, whereby a two phase reaction mixture is produced comprising an aqueous-ammoniacal phase and an organic phase, said organic phase is separated from said aqueous-ammoniacal phase, and said organic phase is subjected to Step (2).

10. The process of claim 9 wherein the volume ratio of ammonia to said organic phase is Step (2) is 1:10 to 1:20.

11. The process of claim 9 wherein water is added to the reaction mixture from Step (1) to promote phase separation.

12. The process of claim 10 wherein an inert organic solvent is added to the reaction mixture from Step (1) to promote phase separation.

13. The process of claim 1 wherein the temperature in Step (1) is from 15° to 70° C.

14. The process of claim 1 wherein said oxo compound also contains another reducible group.

15. The process of claim 14 wherein said oxo compound is isophoronenitrile.

16. The process of claim 1 wherein Step (2) is conducted in the gas phase.

17. The process of claim 1 wherein Step (2) is conducted in the liquid phase with said Schiff base dissolved in an inert organic solvent.

18. The process of claim 1 wherein Step (2) is conducted at a temperature above room temperature and pressure above one atmosphere.

19. The process of claim 18 wherein in step (2) the temperature is from 80° to 200° C. and the pressure is from 80 to 300 bar.

20. The process of claim 1 wherein said hydrogen catalyst contains cobalt, nickel, iron, or a noble metal.

21. The process of claim 1 wherein said hydrogenation catalyst contains cobalt or nickel.

22. The process of claim 18 wherein Step (2) is conducted by a batch process.

23. The process of claim 18 wherein Step (2) is conducted by a continuous process.

24. The process of claim 1 wherein the process is carried out continuously in a reactor having a first section packed with imine-forming catalyst and a second section packed with hydrogenation catalyst.

25. The process of claim 24 wherein said oxo compound and ammonia are introduced into the first section of said reactor in a volume ratio of from 1:10 to 1:20 and hydrogen is introduced into said reactor between said first section and said second section.

26. The process of claim 24 wherein said oxo compound and ammonia are introduced into said first section in a volume ratio from 1:10 to 1:20 and hydrogen is introduced into the first section of said reactor.

27. The process of claim 1 wherein the process is carried out continuously in a reactor containing a mixture of imine-forming catalyst and hydrogenation catalyst.

28. The process of claim 27 wherein said oxo compound and ammonia are initially introduced into said reactor in a volume ratio of from 1:10 to 1:20 and hydrogen is subsequently introduced into said reactor.

29. The process of claim 27 wherein said oxo compound and ammonia are introduced into said reactor in a volume ratio of from 1:10 to 1:20 and hydrogen is introduced simultaneously with said oxo compound and ammonia.

* * * * *